United States Patent [19]

Söderström

[11] 4,362,508
[45] Dec. 7, 1982

[54] METHOD AND AN APPARATUS FOR THE PRODUCTION OF A CORE FOR A ROOT-FILLED PREPARED TOOTH

[76] Inventor: Inge R. Söderström, Mell. Stenbocksgatan 45 a, S-252 42 Helsingborg, Sweden

[21] Appl. No.: 240,095

[22] Filed: Mar. 3, 1981

[30] Foreign Application Priority Data

Mar. 5, 1980 [SE] Sweden .............................. 8001699

[51] Int. Cl.³ .............................................. A61C 5/02
[52] U.S. Cl. ........................................ 433/81; 433/40; 433/220; 433/224
[58] Field of Search .................... 433/81, 40, 220, 224

[56] References Cited

U.S. PATENT DOCUMENTS 2,349,607 5/1944 Berger ................................... 433/40
3,949,748 4/1976 Malmin ................................. 433/81

Primary Examiner—Robert Peshock
Attorney, Agent, or Firm—Fleit & Jacobson

[57] ABSTRACT

For the production of a core for a root-filled prepared tooth the root canal (11) of the prepared tooth (10) is filled with an impression material (27) which is injected at the bottom of the root canal to successively fill the root canal from the bottom thereof and outwardly under expulsion of air therefrom. The injection is carried out with the aid of an injection needle (23) with an injection syringe cylinder (24) with piston (25) attached thereto, the cylinder being filled with said impression material and the injection needle serving as reinforcing element for the impression material, permitting extraction of the cast from the root canal after the impression material has set. In addition to the injection needle with the syringe cylinder and piston attached thereto the apparatus may comprise a mould (13, 14) formed as a guide for the injection needle (23) and adapted to be applied to the prepared tooth (10) for taking a simultaneous cast of the root canal (11) and the free prepared tooth surface (12) of the tooth.

14 Claims, 8 Drawing Figures

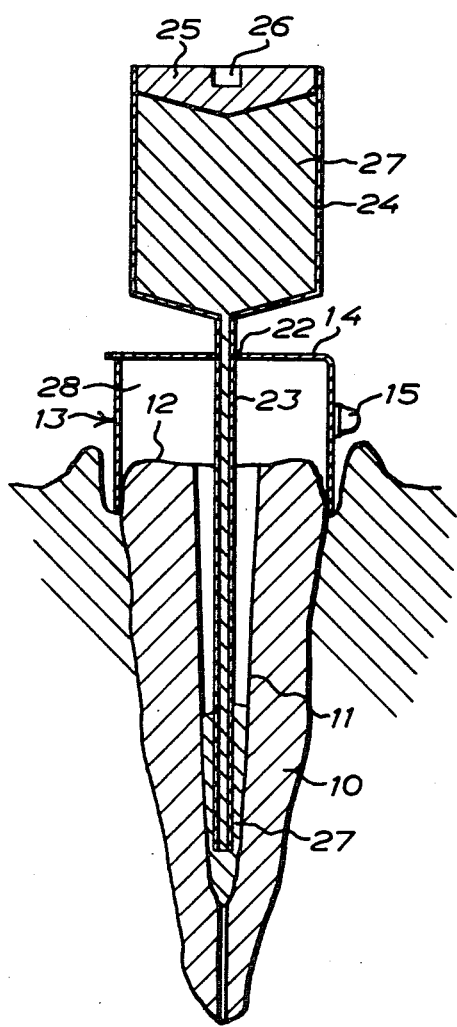
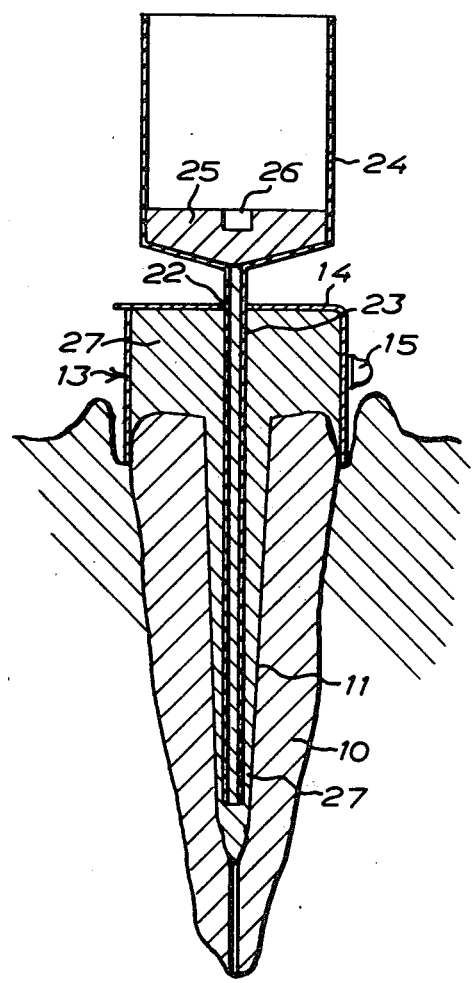

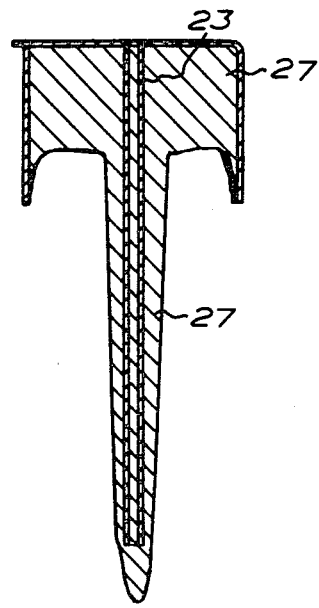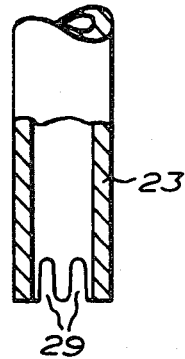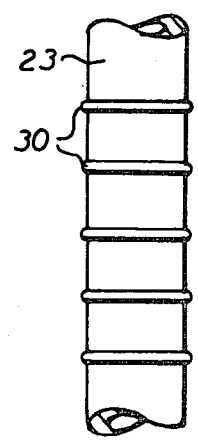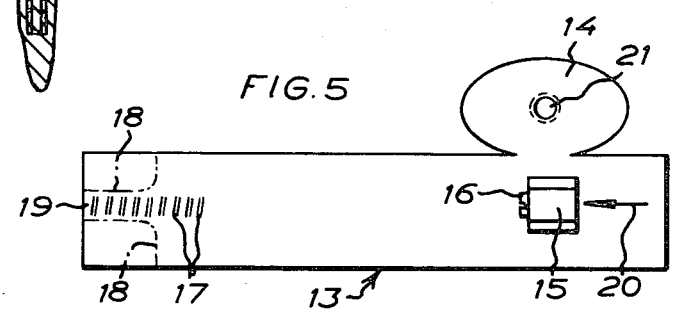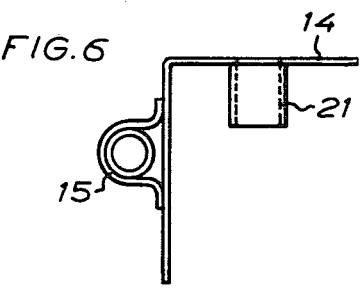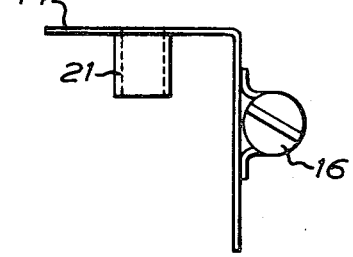

METHOD AND AN APPARATUS FOR THE PRODUCTION OF A CORE FOR A ROOT-FILLED PREPARED TOOTH

This invention relates to a method of producing a core for a root-filled prepared tooth, in which the prepared root canal of the tooth is filled with a preferably gasifiable impression material which is reinforced with a reinforcing element and after setting is extracted from the root canal by means of the reinforcing element.

When it is desired to provide a root-filled tooth with an artificial crown, the conventional procedure applied since long is to use a core as a replacement for lost tooth substance and as a fixation for the artificial crown. On forming such a core it is essential that the usually reamed tooth pulp is filled out to as large an extent as possible to provide a reliable fixation in the remaining portions of the tooth and to obtain maximum strength of the root-filled tooth provided with an artificial crown. It is therefore of great importance that on production of such a core one can make an exact cast of the reamed root canal and the other prepared surfaces of the prepared tooth.

The production of cores for root-filled teeth is therefore time-consuming both to the dentist and the dental technician, and it is difficult to attain a maximum fit of the core in the prepared root canal.

The most customary way of making a cast of the reamed root canal of a root-filled tooth is for the dentist to introduce by means of some tool, usually a pointed piece of metal wire, a thermoplastic impression material in the root canal, after the material has been heated to a soft and deformable state. Once the impression material has set sufficiently, the cast is retracted with the aid of the insertion wire remaining in the impression material. Taking the cast in this way, it very often happens that the cast is unsatisfactory and has to be made over again.

British patent specification No. 1,175,150 discloses such a root filling method, in which a needle shaped tool is utilized to introduce impression material into the reamed root canal. It has however proved that it is difficult, also with the use of such a tool, to provide an exact cast of the root canal. It is also known to introduce impression wax into the reamed root canal by means of a pin. This is shown in U.S. Pat. No. 977,558. This prior art method suffers from the same drawbacks as those described above.

The above-mentioned drawbacks can be avoided by applying the present invention. The present invention thus provides a method of the type indicated in the introduction, and according to the invention this method is characterised in that the reinforcing element is formed as an injection needle having an injection syringe cylinder and piston assembly filled with impression material attached thereto and that the impression material, after the injection needle of the reinforcing element has been introduced into the root canal, is injected at the bottom of the root canal to successively fill the root canal from the bottom and outwardly under expulsion of air therefrom. It is particularly advantageous if a thermoplastic or preferably liquid self-curing plastic material is injected with the injection needle. To further increase the bond between the injection needle serving as a reinforcing element and the impression material it is preferred to form the outer side of the injection needle with a retention-increasing surface structure.

In a further development of the invention it is possible to make a cast not only of the root canal proper but also of the other prepared surface of the tooth. In this further embodiment of the invention there is formed a mould cavity on the free surface of the prepared tooth in that the tooth is surrounded with a tightening strap having a cover with a hole therein for passing the injection needle therethrough, the injection of impression material via the injection needle being caused to continue until both the root canal and said mould cavity have been filled with impression material.

The invention also provides an apparatus for realizing the above described method. Said apparatus comprises an injection needle with a syringe cylinder and piston assembly attached thereto for injection of an impression material in said cylinder into the reamed root canal of a root-filled prepared tooth to provide a cast thereof, and the apparatus is characterised in that the injection needle is formed as a reinforcing element remaining in the future cast and that the apparatus comprises a mould formed as a guide for the reinforcing element and adapted to be placed on the prepared tooth to provide a simultaneous cast of the root canal and the free prepared tooth surface.

The invention will be described in greater detail below with reference to the accompanying drawings in which FIG. 1 shows greatly enlarged and diagrammatically a tooth reamed for an avital core while a cast of the root canal and the prepared tooth surface is taken;

FIG. 2 shows the same tooth as in FIG. 1 after all impression material has been injected;

FIG. 3 shows the cast removed from the tooth;

FIG. 4 shows greatly enlarged the tip of an injection needle which is part of the apparatus according to the invention;

FIG. 5 diagrammatically shows a mould being part of the apparatus according to the invention in a developed state;

FIGS. 6 and 7 show the mould from the right and the left, respectively, with regard to FIG. 5 after a cover of the apparatus has been lowered into operating position;

FIG. 8 shows an example of a retention-increasing surface structure for the outer side of the injection needle.

FIG. 1 shows a tooth 10 the root canal 11 of which has been reamed for accommodating an avital core and the free tooth surface 12 of which has also been prepared for fixation of an artificial crown. A tightening strap 13 having a cover 14 has been tightened about the free visible end of the tooth. The strap 13 is shown more in detail in FIGS. 5–7. The strap is formed approximately as a hose clip and has a tightening screw 16 mounted in a casing 15 which is adapted to cooperate with embossed threads 17 on the strap. In use the length of the strap is fitted to the circumference of the tooth concerned, the dentist cutting away a suitable piece, for instance along the dash lines 18, so that a threaded strap tongue 19 is formed at the end of the strap. Said tongue can of course also have been formed beforehand. The strap is then swept around the tooth and the tongue 19 is inserted in the direction of the arrow 20 for engagement with the tightening screw 16. The strap will thus function as a so-called copper ring, but as distinct from a conventional copper ring it may be fitted exactly to the individual circumference of the tooth. Then the cover 14 is lowered, as illustrated in FIG. 1. In the embodiment illustrated in FIGS. 5–7 the cover has a guide socket 21, but in the embodiment according to FIG. 1 there is only provided a through hole 22.

As will appear from FIG. 1, an injection needle 23 with a syringe cylinder 24 attached thereto has been lowered into the reamed root canal 11 so that the tip of the needle is as close as possible to the bottom of the root canal. The syringe cylinder 24 has a piston 25 with a fixation hole 26 for a piston rod (not shown). The syringe cylinder is filled with a thermoplastic or liquid or semi-liquid self-curing impression material 27.

As will appear from FIG. 1, the impression material which is liquid or has been heated into a liquid state, is injected at the bottom of the reamed root canal 11 so that the impression material is successively urged upwardly through the root canal to gradually fill out entirely the root canal and the cavity 28 defined by the strap and the cover 14 with impression material. By the existence of the cover 14, which thus largely seals the mould cavity 28, there is built up a sufficient backpressure in order that on injection of impression material the mould cavity 28 shall be fully satisfactorily filled out and a cast be taken also of the free prepared tooth surface 12.

After the impression material has been fully injected in the manner illustrated in FIG. 2 and has also set, the cast is retracted from the root canal with the aid of the syringe 23, 24 now serving as a reinforcing element. The injection needle 23 of the syringe remains in the taken impression as a reinforcement thereof, as is illustrated in FIG. 3, where the syringe cylinder 24 with its piston 25 has been removed. In order to further increase the bond between the impression material and the injection needle 23, the latter, as shown in FIG. 8, may have a retention-increasing surface structure on its outer side. In FIG. 8 is shown a surface structure in the form of annular ridges 30, but any other structure increasing the retention may be utilized, such as knurling, roughing etc.

To ensure that the impression material which has been brought into a plastic or liquid state shall be fully satisfactorily ejected at the bottom of the root canal, the injection needle may preferably be formed with slots 29 at the tip, as illustrated in FIG. 4.

The cast taken of the tooth and its root canal in the manner suggested according to the present invention is then used for the production of a core in conventional manner. As the impression material has been injected starting from the bottom of the reamed root canal, the cast will be in the form of a very true copy of the root canal, thus making it possible to produce a core of very good fit. Moreover, it will be possible for the dentist to take the cast much more rapidly since he only needs to select and fasten a tightening strap of suitable size and select a sufficiently large, standardized impression syringe with an injection needle 23 serving as reinforcing element.

The injection syringe 23, 24 may have been formed from some suitable metallic material, such as aluminium or some easy-to-melt metal alloy, but it is also possible to use a plastic of suitable hardness. The last mentioned variant may provide the further advantage that the plastic utilized may be gasifiable so that on producing the core the dental technician can gasify both the impression material 27 and the remaining parts of the injection needle 23 when he manufactures his mould for the metallic core. The same effect can be obtained if the needle of the injection syringe is made from an easy-to-melt metal alloy which is molten and poured out of the mould manufactured by the dental technician for the core.

To facilitate the removal of the cast formed, the inner side and the free prepared surface 12 of the tooth may in conventional manner have been lubricated beforehand with a thin layer of some suitable lubricant, such as vaseline.

I claim:

1. An apparatus for the production of a cast for a mould for a core for a root-filled prepared tooth, comprising: an injection needle, a syringe cylinder connected to an inlet end of the injection needle, a piston movable in said cylinder for injection of an impression material in said cylinder into a reamed root canal of a tooth prepared for root filling, to make a cast thereof, the injection needle forming a reinforcing element remaining in the impression material during and after solidification, and a mould formed as a guide for the reinforcing element and adapted to be applied to the prepared tooth for taking a simultaneous cast of the root canal and the free prepared tooth surface.

2. An apparatus as claimed in claim 1, wherein the mould consists of a tightening strap formed so as to be tightened around the tooth and exactly fitted to the individual circumference of the tooth, said strap being provided with a cover with a hole therein for passing the injection needle therethrough.

3. An apparatus as claimed in claim 1 or 2, wherein the piston of the syringe cylinder has a hole for accommodating a piston rod.

4. An apparatus as claimed in claim 1 or 2, wherein the injection needle serving as a reinforcing element has a retention-increasing surface structure on its outer side.

5. An apparatus as claimed in claim 4, wherein the injection needle serving as a reinforcing element is formed with at least one recess at the edge of the needle tip.

6. An apparatus according to claim 1, wherein said injection needle is formed of an easy-to-melt metal alloy.

7. An apparatus according to claim 1, wherein said injection needle is formed of a gasifiable material, and the solidified impression materials a gasifiable material so that both the injection needle and impression material are gasified during production of the mould for the core.

8. A method of producing a mould for a core for a crown insertable into a prepared root canal, said method comprising "positioning a mould for a crown on a tooth,":

positioning an outlet end of an injection needle within the tooth and in close proximity to the bottom of the prepared root canal, the injection needle extending through the mould and having an inlet end connected to a cylinder containing a flowable impression material;

moving a piston within the cylinder to inject the impression material into the root canal while maintaining the outlet end of the injection needle in close proximity to the bottom of the root canal so that the injected material progressively fills the root canal from the bottom thereof outwardly;

leaving the injection needle in the root canal while the injected material solidifies to produce a cast for the crown and a mould for a core for insertion into the root canal, the injection needle forming a reinforcing element for the cast; and removing the solidified material and injection needle as a single unit from the root canal.

9. A method according to claim 8, wherein the solidified material is gasifiable upon the application of heat during formation of the mould from the removed solidified material.

10. A method according to claim 8 or 9, wherein the impression material is thermoplastic.

11. A method according to claim 8 or 9, wherein the impression material is self-curing after injection into the root canal.

12. A method according to claim 8 further comprising forming a mould cavity on the free surface of the tooth by surrounding the tooth with a tightening cap having a cover with a hole therein for passing the injection needle therethrough, the injection of impression material via the injection needle continuing until both the root canal and said mould cavity have been filled with the impression material.

13. A method according to claim 9, wherein the injection needle is made of an easy-to-melt metal alloy, said method further comprising melting said needle during formation of the mould for the core.

14. A method according to claim 9, wherein the injection needle is made of a gasifiable material, said method further comprising gasifying said needle during formation of the mould for the core.

* * * * *